(12) United States Patent
Nayak K et al.

(10) Patent No.: US 10,881,362 B2
(45) Date of Patent: Jan. 5, 2021

(54) SYSTEMS FOR LASER ALIGNMENT

(71) Applicant: General Electric Company, Schenectady, NY (US)

(72) Inventors: Vishwanath Nayak K, Bangalore (IN); Saiesh Raiker, Bangalore (IN); Dhaval Pravinbhai Dangashiya, Bangalore (IN)

(73) Assignee: General Electric Company, Schenectady, NY (US)

( * ) Notice: Subject to any disclaimer, the term of this patent is extended or adjusted under 35 U.S.C. 154(b) by 44 days.

(21) Appl. No.: 16/197,205

(22) Filed: Nov. 20, 2018

(65) Prior Publication Data
US 2020/0155111 A1 May 21, 2020

(51) Int. Cl.
*A61B 6/03* (2006.01)
*A61B 6/08* (2006.01)
*A61B 6/04* (2006.01)
*A61B 6/00* (2006.01)

(52) U.S. Cl.
CPC ............... *A61B 6/08* (2013.01); *A61B 6/032* (2013.01); *A61B 6/035* (2013.01); *A61B 6/04* (2013.01); *A61B 6/0407* (2013.01); *A61B 6/0487* (2020.08); *A61B 6/40* (2013.01); *A61B 6/4007* (2013.01); *A61B 6/4014* (2013.01); *A61B 6/44* (2013.01); *A61B 6/4429* (2013.01); *A61B 6/4435* (2013.01); *A61B 6/46* (2013.01); *A61B 6/461* (2013.01); *A61B 6/467* (2013.01); *A61B 6/469* (2013.01); *A61B 6/482* (2013.01); *A61B 6/587* (2013.01)

(58) Field of Classification Search
CPC ........... A61B 6/032; A61B 6/035; A61B 6/04; A61B 6/0407; A61B 6/0457; A61B 6/08; A61B 6/40; A61B 6/4007; A61B 6/4014; A61B 6/44; A61B 6/4429; A61B 6/4435; A61B 6/46; A61B 6/461; A61B 6/467; A61B 6/469; A61B 6/482
USPC ............... 378/9, 20, 196–198, 205–207, 209
See application file for complete search history.

(56) References Cited

U.S. PATENT DOCUMENTS

| 4,972,062 A | 11/1990 | Aharon | |
| 5,533,082 A * | 7/1996 | Grönemeyer | A61B 6/035 378/20 |
| 5,553,112 A * | 9/1996 | Hardy | A61B 6/08 378/206 |
| 5,598,269 A * | 1/1997 | Kitaevich | A61B 6/08 356/399 |
| 5,782,842 A * | 7/1998 | Kloess | A61B 17/3403 378/206 |

(Continued)

FOREIGN PATENT DOCUMENTS

| JP | 2008522233 A | 6/2008 |
| WO | 2017167687 A2 | 10/2017 |

*Primary Examiner* — Allen C. Ho

(57) ABSTRACT

Various methods and systems are provided for laser alignment systems, particularly laser alignment systems of medical imaging systems. In one example, a medical imaging system comprises: a gantry; and a laser mount including: a first section fixedly coupled to the gantry; a second section seated within the first section and slideable within the first section; and a third section seated within the second section and rotatable within the second section, the third section adapted to house a laser radiation source.

9 Claims, 7 Drawing Sheets

(56) References Cited

U.S. PATENT DOCUMENTS

| | | | | |
|---|---|---|---|---|
| 6,009,147 A * | 12/1999 | Stein | A61B 6/0421 | 378/146 |
| 6,041,249 A * | 3/2000 | Regn | A61B 6/08 | 378/20 |
| 6,048,097 A * | 4/2000 | Heinze | A61B 6/08 | 378/205 |
| 6,079,876 A * | 6/2000 | Schuetz | A61B 6/08 | 378/205 |
| 6,435,717 B1 * | 8/2002 | Köhler | A61B 6/107 | 378/205 |
| 7,016,453 B2 * | 3/2006 | Ruimi | A61B 6/032 | 378/114 |
| 7,465,090 B2 * | 12/2008 | Haras | A61B 6/08 | 378/206 |
| 7,488,108 B2 * | 2/2009 | Pommi | A61B 6/469 | 378/205 |
| 7,603,163 B2 * | 10/2009 | McNeirney | A61B 6/08 | 378/205 |
| 7,632,015 B2 * | 12/2009 | Stayman | A61B 6/032 | 378/163 |
| 7,677,801 B2 * | 3/2010 | Pakzaban | A61B 5/103 | 378/162 |
| 7,695,192 B2 * | 4/2010 | Henderson | A61B 6/037 | 378/198 |
| 7,697,147 B2 * | 4/2010 | Kindlein | A61B 6/08 | 356/601 |
| 7,720,196 B2 * | 5/2010 | Zhang | A61B 5/113 | 378/65 |
| 7,766,723 B2 | 8/2010 | Mazoyer | | |
| 7,798,709 B2 * | 9/2010 | Haras | A61B 6/032 | 378/206 |
| 8,155,729 B1 * | 4/2012 | Hsieh | A61B 34/20 | 600/410 |
| 8,182,149 B2 * | 5/2012 | Haras | A61B 17/3403 | 378/205 |
| 8,198,579 B2 * | 6/2012 | Jeung | A61B 6/08 | 250/252.1 |
| 8,506,163 B2 * | 8/2013 | Shinno | A61B 6/032 | 378/206 |
| 8,509,381 B2 * | 8/2013 | Walker | A61B 6/14 | 378/196 |
| 8,526,573 B2 * | 9/2013 | Ferro, Jr. | A61B 6/566 | 378/98 |
| 8,692,181 B2 * | 4/2014 | Gross | A61B 6/547 | 250/221 |
| 9,055,874 B2 * | 6/2015 | Van Kampen | A61B 6/032 | |
| 9,277,895 B2 * | 3/2016 | Hara | A61B 6/0407 | |
| 9,433,395 B2 * | 9/2016 | Kang | A61B 6/544 | |
| 9,477,312 B2 * | 10/2016 | Hoang | G06F 3/017 | |
| 9,521,982 B2 * | 12/2016 | Hsieh | G02B 26/023 | |
| 9,532,727 B2 * | 1/2017 | Herold | A61B 5/055 | |
| 9,622,713 B2 * | 4/2017 | Xu | G01R 33/28 | |
| 9,662,076 B2 * | 5/2017 | Jia | A61B 6/08 | |
| 9,687,203 B2 * | 6/2017 | Smith | A61B 6/0492 | |
| 9,743,893 B2 * | 8/2017 | Inglese | A61B 6/14 | |
| 9,763,599 B2 * | 9/2017 | Graumann | A61B 5/0073 | |
| 9,795,347 B2 * | 10/2017 | Jan | A61B 6/025 | |
| 9,867,582 B2 * | 1/2018 | Kim | A61B 6/08 | |
| 9,924,872 B2 * | 3/2018 | Harada | A61B 6/08 | |
| 9,924,911 B2 * | 3/2018 | Heath | A61B 6/06 | |
| 9,931,088 B2 * | 4/2018 | Grasruck | A61B 6/08 | |
| 9,943,271 B2 * | 4/2018 | Dirauf | A61B 6/0492 | |
| 10,016,171 B2 * | 7/2018 | Fortuna | A61B 6/4447 | |
| 10,076,290 B2 * | 9/2018 | Lee | A61B 6/58 | |
| 10,098,609 B2 * | 10/2018 | Kim | A61B 6/06 | |
| 10,188,358 B2 * | 1/2019 | Levin | A61B 5/0037 | |
| 10,188,365 B2 * | 1/2019 | Lee | A61B 6/4417 | |
| 10,265,042 B2 * | 4/2019 | Stoutenburgh | A61B 6/542 | |
| 10,321,880 B2 * | 6/2019 | Lerch | A61B 6/0407 | |
| 10,335,096 B2 * | 7/2019 | Nett | A61B 6/5205 | |
| 10,376,217 B2 * | 8/2019 | Schmidt | A61B 6/54 | |
| 10,383,593 B2 * | 8/2019 | Jung | A61B 6/542 | |
| 10,390,776 B2 * | 8/2019 | Fuh | A61B 6/42 | |
| 10,424,118 B2 * | 9/2019 | Hannemann | A61B 5/00 | |
| 10,512,417 B2 * | 12/2019 | Hannemann | A61B 5/055 | |
| 10,537,298 B2 * | 1/2020 | Martino | A61B 6/04 | |
| 10,542,957 B2 * | 1/2020 | Sawanobori | A61B 6/54 | |
| 10,548,482 B2 * | 2/2020 | Lerch | A61B 1/07 | |
| 10,561,391 B2 * | 2/2020 | Nett | A61B 6/027 | |
| 10,568,596 B2 * | 2/2020 | Liu | A61B 6/032 | |
| 10,607,099 B2 * | 3/2020 | Cai | A61B 6/584 | |
| 10,610,170 B2 * | 4/2020 | Lin | A61B 6/545 | |
| 10,610,185 B2 * | 4/2020 | Taguchi | A61B 6/032 | |
| 10,631,799 B2 * | 4/2020 | Rahmes | A61B 6/145 | |
| 10,638,985 B2 * | 5/2020 | Yu | A61B 6/0492 | |
| 10,653,377 B2 * | 5/2020 | Ito | A61B 5/0091 | |
| 10,660,583 B2 * | 5/2020 | Haider | A61B 6/0487 | |
| 10,660,593 B2 * | 5/2020 | Gao | A61B 6/12 | |
| 10,667,869 B2 * | 6/2020 | Kotian | A61B 90/13 | |
| 10,674,975 B2 * | 6/2020 | Gao | A61B 6/4411 | |
| 10,674,976 B2 * | 6/2020 | Gao | A61B 6/4447 | |
| 10,722,200 B2 * | 7/2020 | Kiraly | A61B 90/35 | |
| 2014/0125577 A1 | 5/2014 | Hoang et al. | | |
| 2018/0134387 A1 | 5/2018 | Kovac et al. | | |

\* cited by examiner

US 10,881,362 B2

SYSTEMS FOR LASER ALIGNMENT

FIELD

Embodiments of the subject matter disclosed herein relate to laser alignment systems, particularly laser alignment systems of medical imaging systems.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

In order to direct the x-rays of a CT system through a target volume (e.g., a patient) for imaging of the target volume, a laser alignment system is often utilized to aid in positioning the target volume within an imaging region of the CT system. The laser alignment system includes lasers that project beams of light toward the imaging region of the CT system. An operator of the CT system may adjust the position of the target volume within the imaging region in order to align a center of the target volume with a location of the imaging region intersected by the beams of light of the laser alignment system.

BRIEF DESCRIPTION

In one embodiment, a medical imaging system comprises: a gantry; and a laser mount including: a first section fixedly coupled to the gantry; a second section seated within the first section and slideable within the first section; and a third section seated within the second section and rotatable within the second section, the third section adapted to house a laser radiation source.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIGS. 4-9 are shown to scale, although other relative dimensions may be used, if desired.

DETAILED DESCRIPTION

Figure 5:
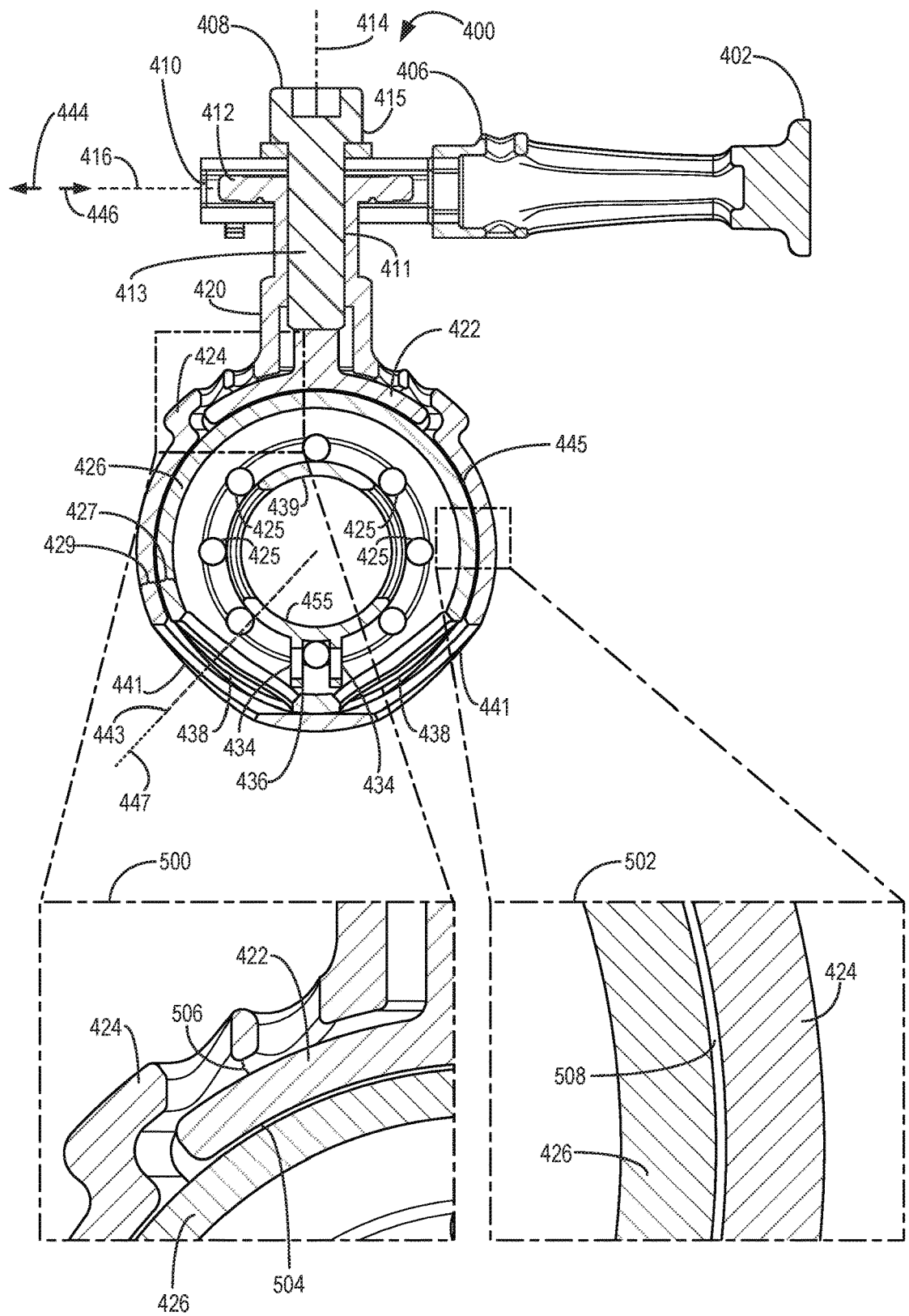
FIG. 5 shows a front cross-sectional view of the laser mount of FIG. 4.
Figure 6:
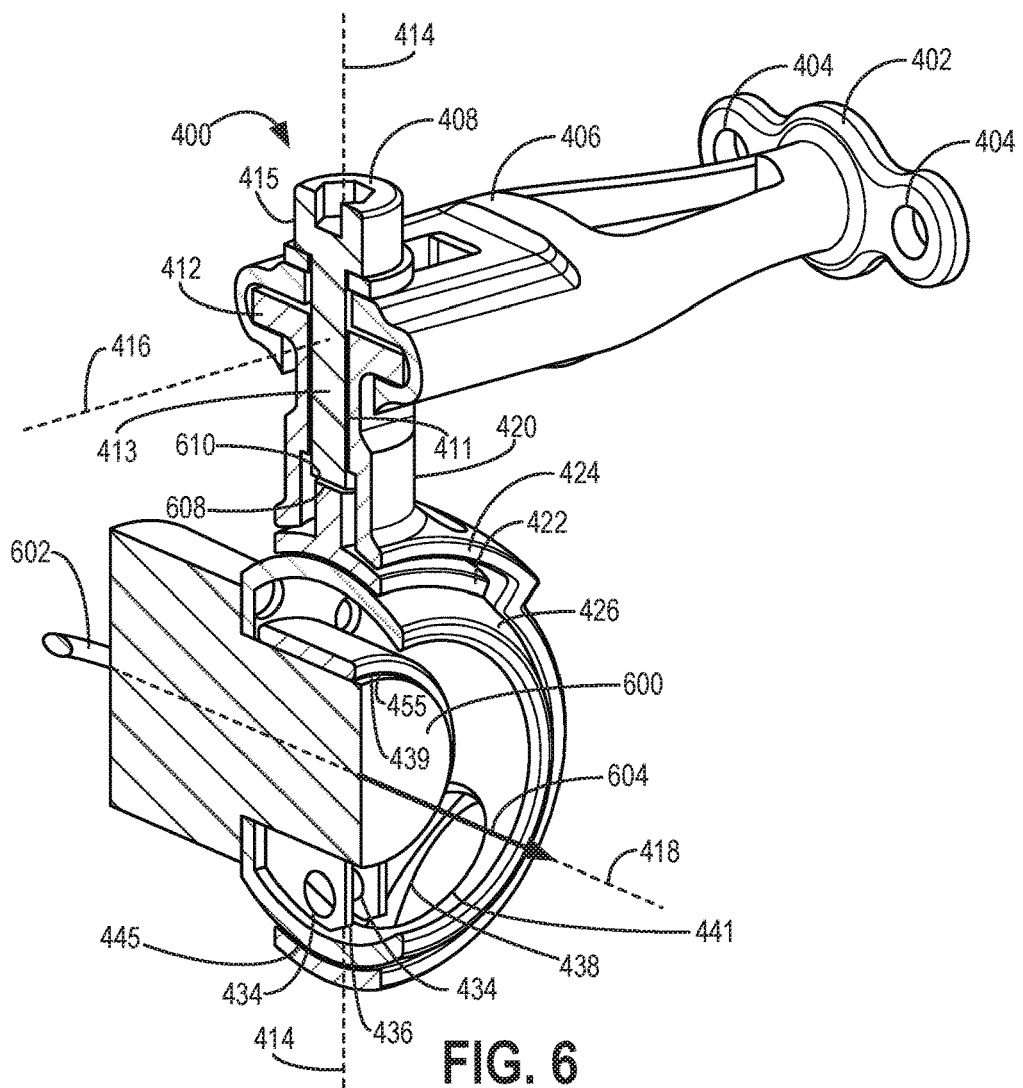
FIG. 6 shows a side perspective cross-sectional view of the laser mount of FIGS. 4-5.
Figure 7:
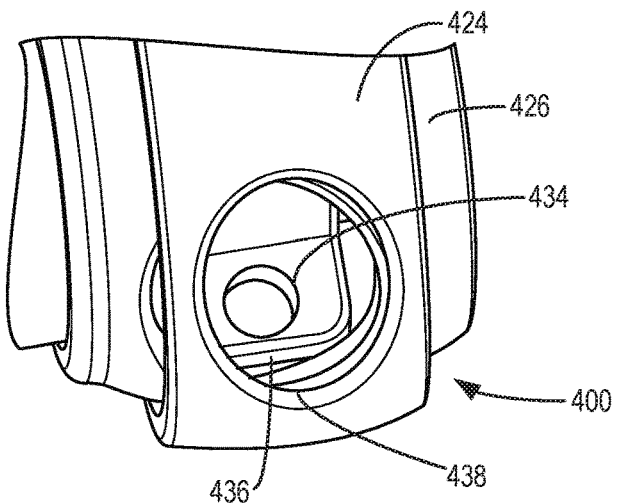
FIG. 7 shows a partial perspective view of a side opening of the laser mount of FIGS. 4-6.
Figure 8:
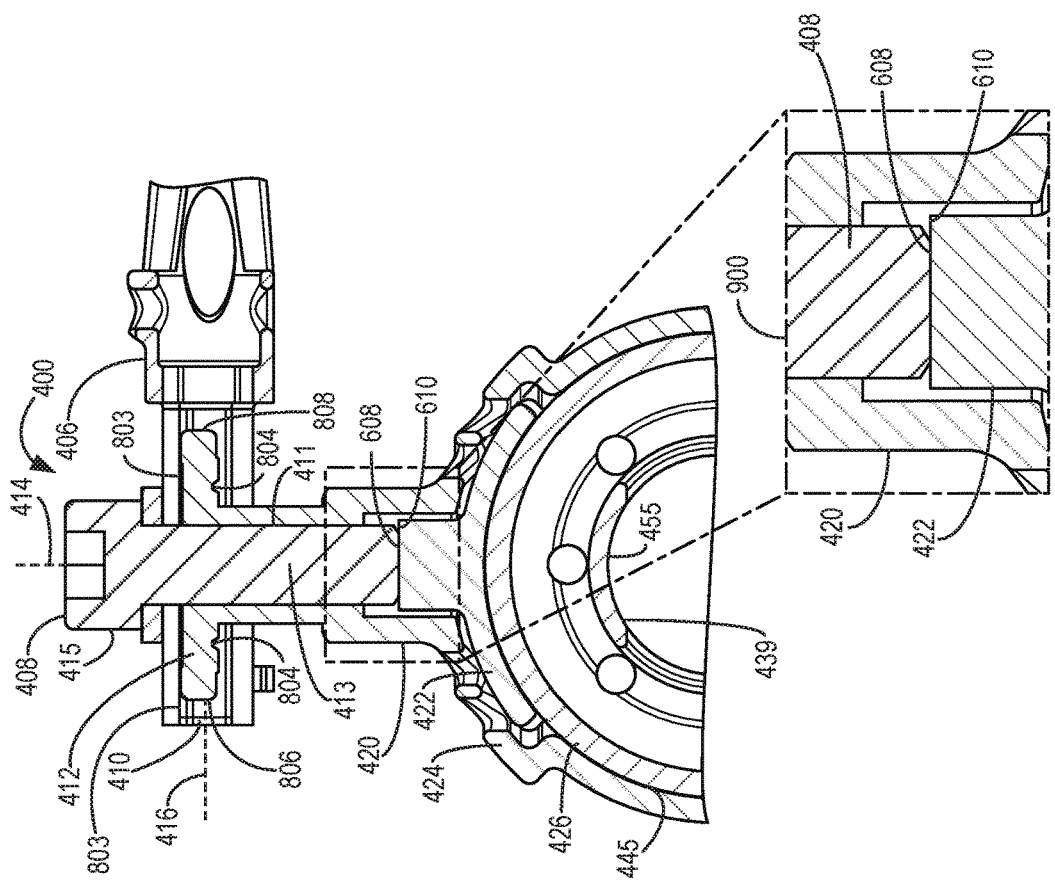
FIG. 8 shows a front cross-sectional view of the laser mount of FIGS. 4-7 in an unlocked configuration.
Figure 9:
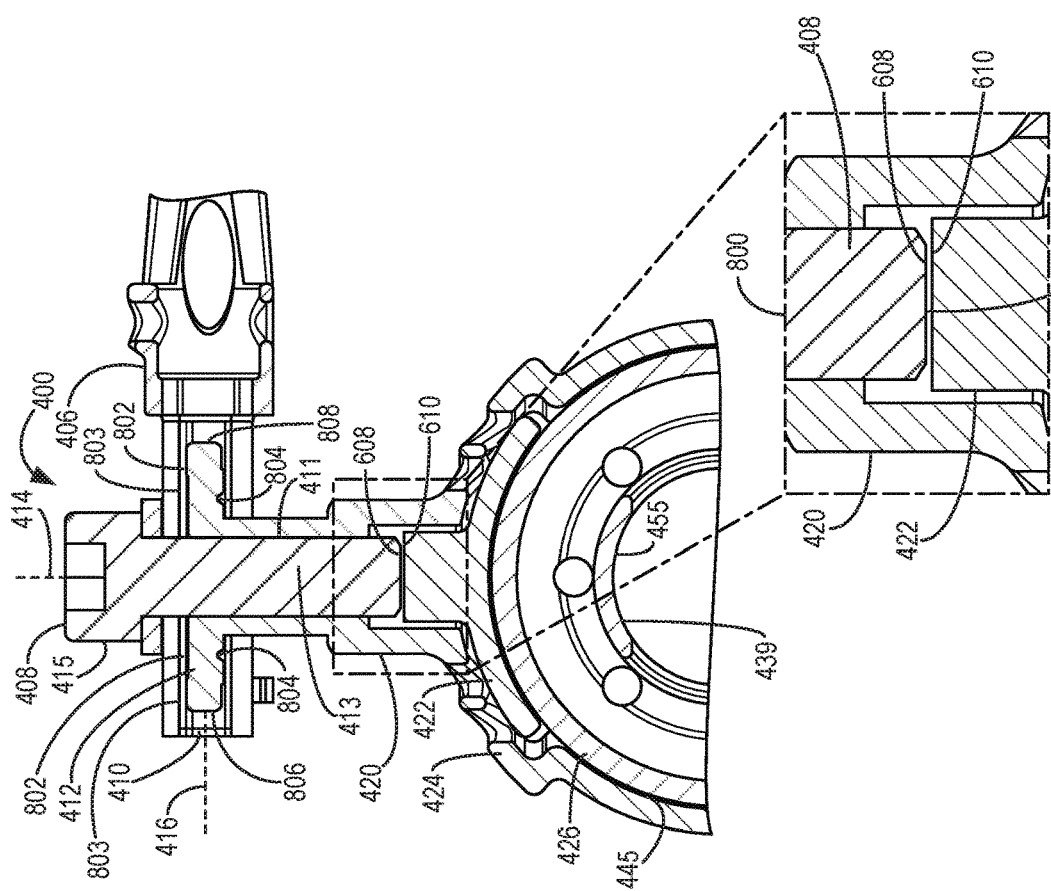
FIG. 9 shows a front cross-sectional view of the laser mount of FIGS. 4-8 in a locked configuration.
Figure 10:
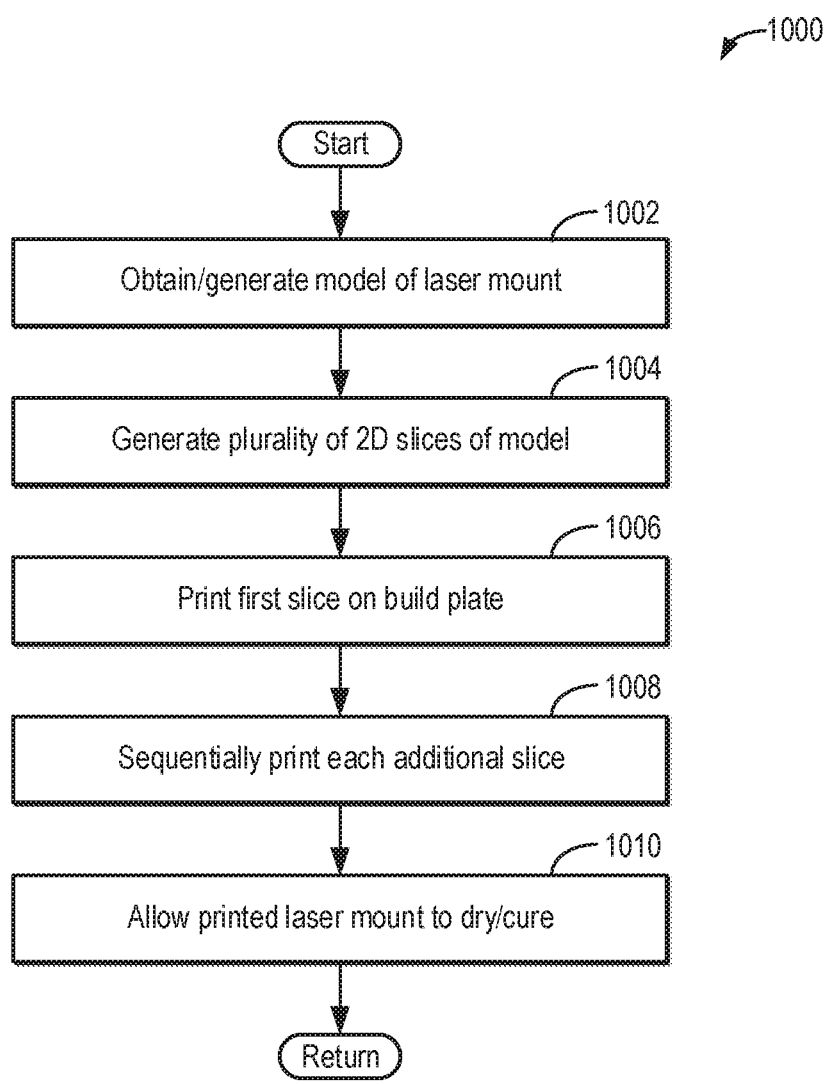
FIG. 10 shows a flowchart illustrating a method for manufacturing a laser mount via an additive manufacturing process.

The following description relates to various embodiments of systems for laser alignment, particularly laser alignment for medical imaging systems. A medical imaging system, such as the medical imaging systems shown schematically by FIGS. 1-2, may include a laser alignment system, such as the laser alignment system shown schematically by FIG. 3. The laser alignment system may include a laser mount, such as the laser mount shown by FIG. 4. An arm of the laser mount may couple to the imaging system, with the arm including a slot adapted to receive a slider element of an outer housing of the laser mount. The position of the outer housing may be adjusted by adjusting the position of the slider element within the slot. The laser mount further includes an inner housing and a lock element each disposed within the outer housing, with the inner housing being rotatable relative to the outer housing and lockable to the outer housing via the lock element. The inner housing includes a clamp accessible via an opening in the outer housing, as shown by FIG. 7. The clamp is adapted to couple with a laser radiation source such as a laser diode, as shown by FIG. 6. In some examples, as illustrated by the flowchart of FIG. 10, the components of the laser mount (e.g., the inner housing, outer housing, etc.) may be formed together from a same 3D model via an additive manufacturing process. In an unlocked configuration, as shown by FIG. 8, the inner housing and lock element are each separated from the outer housing by respective clearances, as shown by FIG. 5. In a locked configuration, as shown by FIG. 9, the lock element engages with the inner housing in order to lock the position of the inner housing relative to the outer housing. In this way, the position of the laser diode relative to the imaging system may be adjusted via rotation of the inner housing within the outer housing and/or adjustment of the position of the slider element within the slot of the arm.

Though a CT system is described by way of example, it should be understood that the present systems and techniques may also be useful when applied to other imaging modalities, such as tomosynthesis, C-arm angiography, and so forth. The present discussion of a CT imaging modality is provided merely as an example of one suitable imaging modality.

Various embodiments may be implemented in connection with different types of imaging systems. For example, various embodiments may be implemented in connection with a CT imaging system in which an x-ray source projects a fan- or cone-shaped beam that is collimated to lie within an x-y plane of a Cartesian coordinate system and generally referred to as an "imaging plane." The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurement from all the detectors is acquired separately to produce a transmission profile.

In some CT systems, the x-ray source and the detector array are rotated with a gantry within the imaging plane and around the object to be imaged such that the angle at which the x-ray beam intersects the object constantly changes. A complete gantry rotation occurs when the gantry concludes one full 360 degree revolution. A group of x-ray attenuation measurements (e.g., projection data) from the detector array at one gantry angle is referred to as a "view." A view is, therefore, each incremental position of the gantry. A "scan" of the object comprises a set of views made at different gantry angles, or view angles, during one revolution of the x-ray source and detector.

In an axial scan, the projection data is processed to construct an image that corresponds to a two-dimensional slice taken through the object. Alternatively, a helical scan may be performed, wherein the patient is moved through an opening of the gantry synchronously with the rotation of the gantry, while the data for the prescribed number of slices is acquired. In order to aid with positioning the patient relative to the gantry to acquire scans of the desired anatomy of the patient to be imaged, CT imaging systems may include a laser alignment system. The laser alignment system may include one or more laser mounts according to the embodiments described herein.

Figure 1:
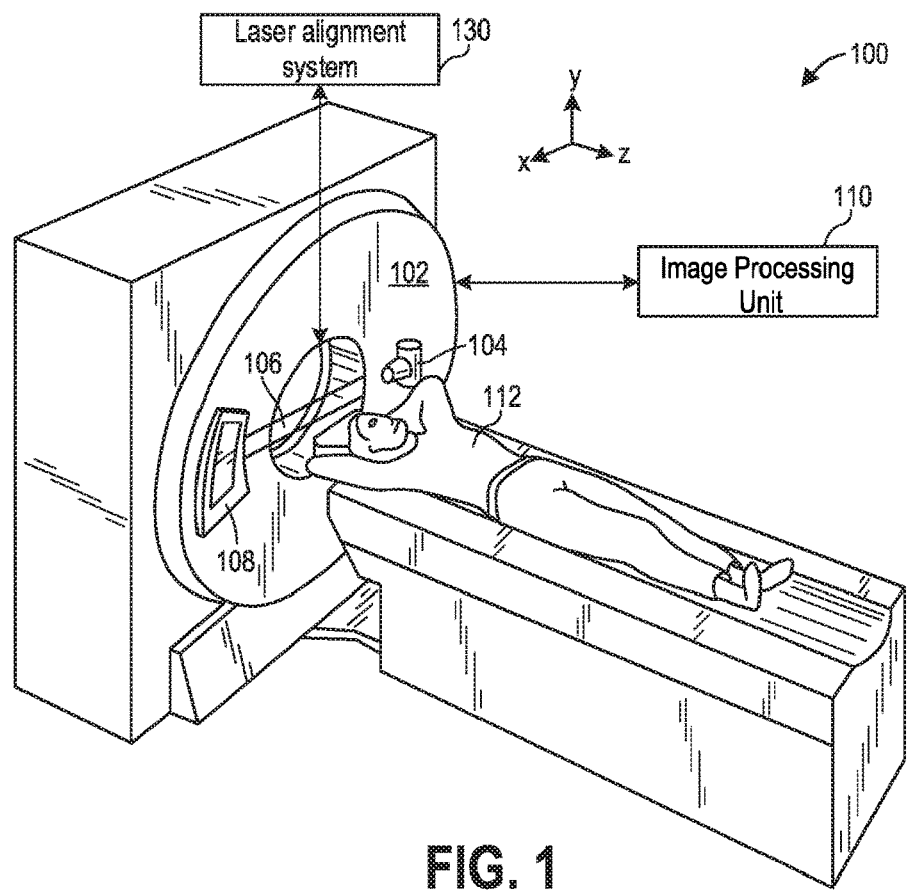
FIG. 1 schematically shows an imaging system including a laser alignment system.

Turning firstly to FIG. 1, CT system 100 is schematically shown. CT system 100 is configured to allow fast and iterative image reconstruction. Particularly, the CT system 100 is configured to image a subject 112 (e.g., a patient, an inanimate object, one or more manufactured parts, and/or foreign objects such as dental implants, stents, and/or contrast agents present within the body). The CT system 100 includes a gantry 102 (e.g., rotatable gantry), which in turn, may further include at least one x-ray radiation source 104 configured to project a beam of x-ray radiation 106 for use in imaging the patient. Specifically, the x-ray radiation source 104 is configured to project the beam of x-ray radiation 106 towards a detector array 108 positioned on the opposite side of the gantry 102. Although FIG. 1 depicts only a single x-ray radiation source 104, multiple x-ray radiation sources 104 may be employed to project a plurality of beams of x-ray radiation 106 for acquiring projection data corresponding to the patient at different energy levels.

The CT system 100 may further include an image processing unit 110 configured to reconstruct images of a target volume of the patient using an iterative or analytic image reconstruction method. For example, the image processing unit 110 may use an analytic image reconstruction approach such as filtered backprojection (FBP) to reconstruct images of a target volume of the patient. As another example, the image processing unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the patient.

CT system 100 includes laser alignment system 130 (indicated schematically in FIG. 1). Laser alignment system 130 includes at least one laser radiation source (e.g., laser diode) configured to produce a beam of visible light (e.g., red light, such as light having a wavelength of approximately 625 nanometers). The beam of visible light produced by each laser radiation source may be utilized by an operator of the CT system 100 (e.g., a radiologist) in order to aid with aligning the area of interest of the subject 112 (e.g., the region of the subject 112 to be imaged by the CT system 100) with the beam of x-ray radiation 106 used to image the subject 112. For example, the beam of visible light produced by each laser radiation source of the laser alignment system 130 may be configured to intersect at a location along a path of the beam of x-ray radiation 106. The operator of the CT system 100 may identify the portion of the subject 112 to be intersected by the beam of x-ray radiation 106 based on the position of the beams of visible light produced by the laser radiation sources of the laser alignment system 103 relative to the subject 112. In one example, each beam of visible light of the laser alignment system 130 may be configured to intersect at a midpoint of gantry 102 (e.g., a location along a central axis of the gantry 102). Further examples of laser alignment systems similar to laser alignment system 103 are described below with reference to FIGS. 2-9.

Figure 2:
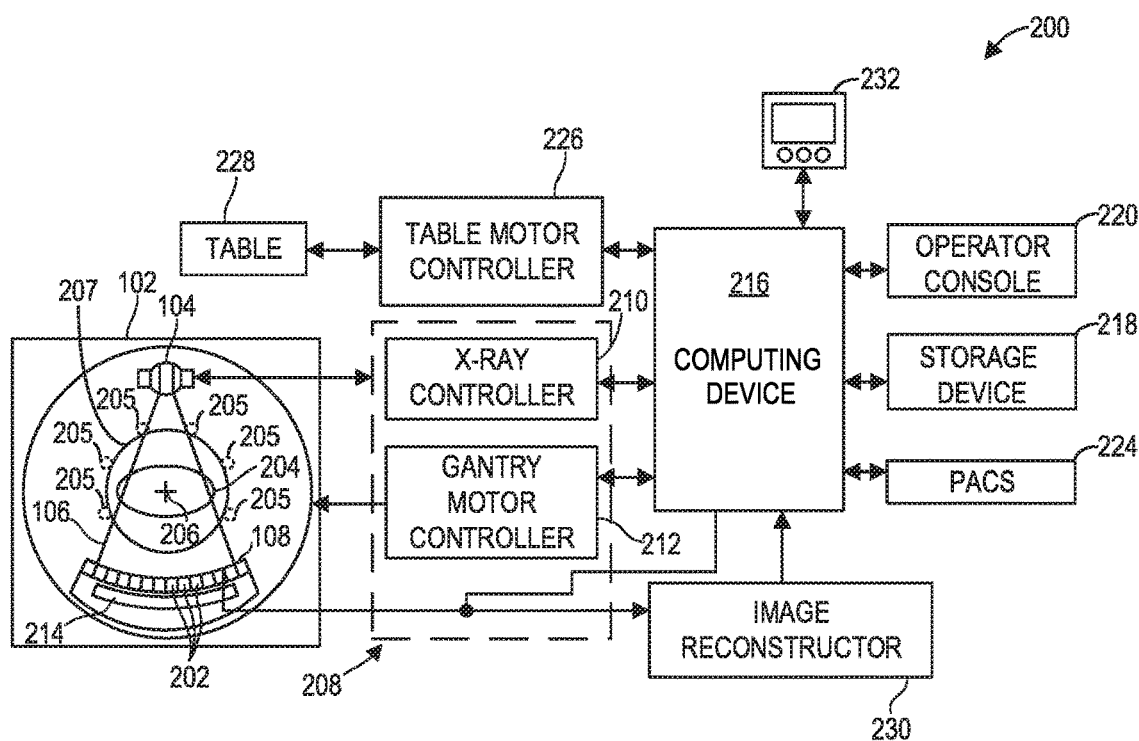
FIG. 2 shows a block schematic diagram of an imaging system including a laser alignment system.

FIG. 2 illustrates an exemplary imaging system 200 similar to the CT system 100 of FIG. 1. In accordance with aspects of the present disclosure, the imaging system 200 is configured to perform automatic exposure control. The imaging system 200 may include the detector array 108 (see FIG. 1). The detector array 108 further includes a plurality of detector elements 202 that together sense the beam of x-ray radiation 106 (see FIG. 1) that pass through a subject 204 such as a patient to acquire corresponding projection data. Accordingly, the detector array 108 may be fabricated in a multi-slice configuration including the plurality of rows of cells or detector elements 202. In such a configuration, one or more additional rows of the detector elements 202 are arranged in a parallel configuration for acquiring the projection data.

The imaging system 200 may be configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, where a projection angle relative to the subject 204 varies as a function of time, the mounted components may be configured to move along a general curve rather than along a segment of a circle.

The imaging system 200 may include a control mechanism 208 to control movement of the components such as rotation of the gantry 102 and the operation of the x-ray radiation source 104. The control mechanism 208 may further include an x-ray controller 210 configured to provide power and timing signals to the x-ray radiation source 104. Additionally, the control mechanism 208 includes a gantry motor controller 212 configured to control a rotational speed and/or position of the gantry 102 based on imaging requirements.

The control mechanism 208 may further include a data acquisition system (DAS) 214 configured to sample analog data received from the detector elements 202 and convert the analog data to digital signals for subsequent processing. The data sampled and digitized by the DAS 214 is transmitted to a computing device (also referred to as processor) 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage device.

Additionally, the computing device 216 provides commands and parameters to one or more of the DAS 214, the x-ray controller 210, and the gantry motor controller 212 for controlling system operations such as data acquisition and/or processing. The computing device 216 may control system operations based on operator input. The computing device 216 receives the operator input, for example, including commands and/or scanning parameters via an operator console 220 operatively coupled to the computing device 216. The operator console 220 may include a keyboard (not shown) or a touchscreen, as non-limiting examples, to allow the operator to specify the commands and/or scanning parameters.

Although FIG. 2 illustrates only one operator console 220, more than one operator console may be coupled to the imaging system 200, for example, for inputting or outputting system parameters, requesting examinations, and/or viewing images. Further, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

For example, the imaging system 200 may either include, or may be coupled to a picture archiving and communications system (PACS) 224. The PACS 224 may be further coupled to a remote system such as a radiology department information system, hospital information system, and/or to an internal and/or external network (not shown) to allow operators at different locations to supply commands and parameters and/or gain access to the image data.

The computing device 216 uses the operator-supplied and/or system-defined commands and parameters to operate a table motor controller 226, which in turn, may control a motorized table 228. Particularly, the table motor controller 226 moves the motorized table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, computing resources in a "cloud" network cluster may be used for the image reconstructor 230.

The image reconstructor 230 may store the images reconstructed in the storage device 218. Additionally or alternatively, the image reconstructor 230 transmits the reconstructed images to the computing device 216 for generating useful patient information for diagnosis and evaluation. The computing device 216 may transmit the reconstructed images and/or the patient information to a display 232 communicatively coupled to the computing device 216 and/or the image reconstructor 230. The display 232 may allow the operator to evaluate the imaged anatomy. The display 232 may also allow the operator to select a volume of interest (VOI) and/or request patient information, for example, via a graphical user interface (GUI) for a subsequent scan or processing.

Imaging system 200 includes a laser alignment system similar to the laser alignment system 130 described above with reference to FIG. 1. Specifically, imaging system 200 includes a plurality of laser radiation sources 205 (e.g., laser diodes) positioned around opening 207 of gantry 102 (e.g., the opening through which the subject 204 to be imaged is positioned). In some examples, each of the laser radiation sources 205 may be configured to produce a beam of visible light directed toward (e.g., intersecting) the center of rotation 206. A plurality of laser radiation sources 205 are shown schematically by FIG. 2. In some examples, each laser radiation source 205 may be positioned entirely within an interior of gantry 102 (e.g., positioned within a housing of the gantry 102, such that each laser radiation source 205 is not visible at an exterior of the housing of the gantry 102), and each beam of visible light produced by laser radiation source 205 may pass through a corresponding aperture of the gantry 102 toward the axis of rotation 206 (e.g., in order to project onto the subject 204 to indicate the position of the subject 204 relative to the gantry 102 and axis of rotation 206). In the example shown by FIG. 2, the laser alignment system includes six laser radiation sources 205. However, in other examples, the laser alignment system may include a different number and/or relative arrangement of laser radiation sources 205 (e.g., three, four, etc.). An example of another laser alignment system similar to the laser alignment system of FIG. 2 and the laser alignment system 130 of FIG. 1 is described below with reference to FIG. 3.

Figure 3:
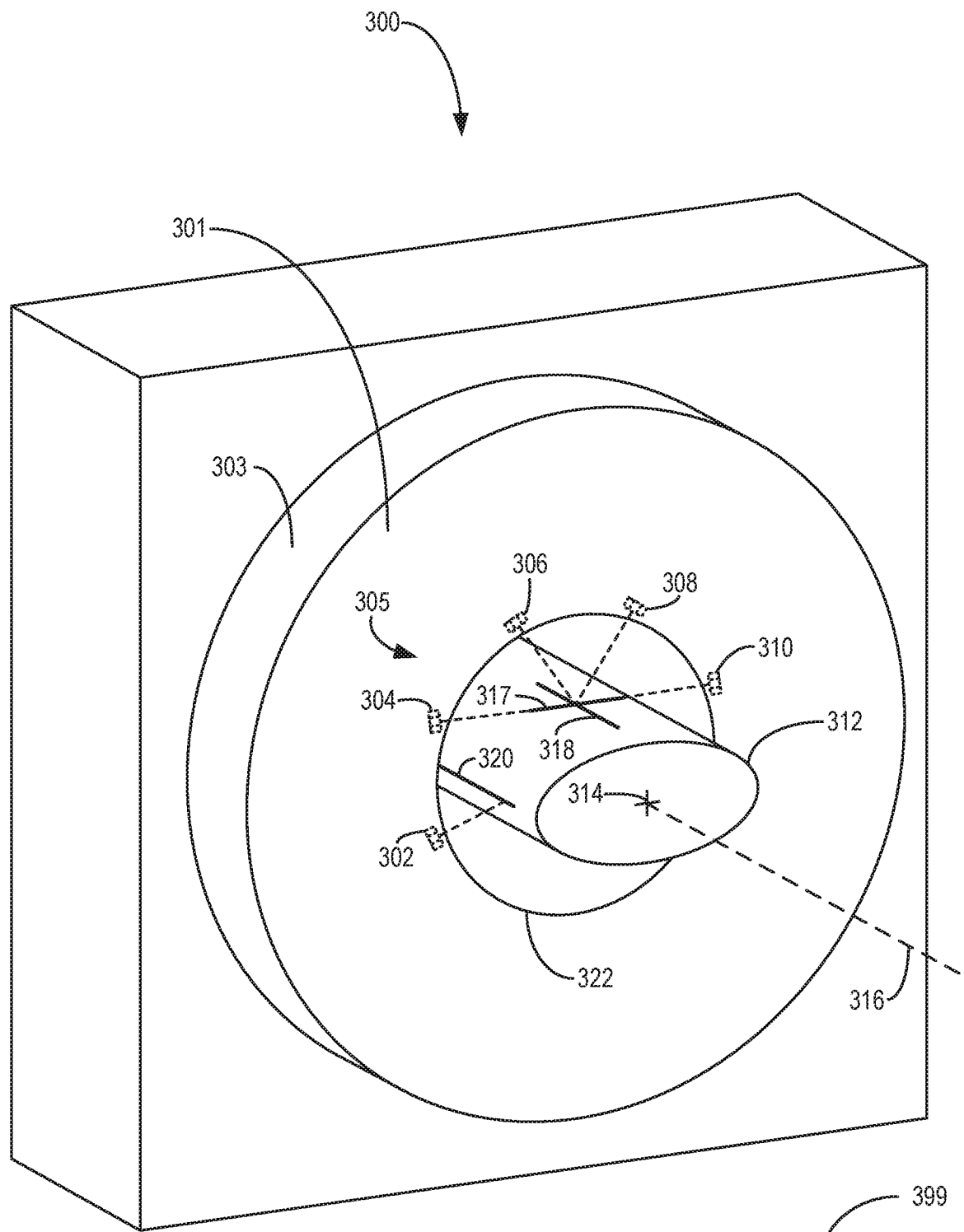
FIG. 3 schematically shows an arrangement of lasers of a laser alignment system relative to a gantry of an imaging system.

FIG. 3 schematically shows another example of a CT imaging system 300, similar to the CT system 100 shown by FIG. 1 and described above and/or the imaging system 200 shown by FIG. 2 and described above. CT imaging system 300 includes gantry 301 (e.g., rotatable gantry), similar to gantry 102 described above. Gantry 301 includes opening 322 adapted to receive a subject 312 (e.g., a patient, indicated schematically in FIG. 3) to be imaged by the CT imaging system 300. For example, CT imaging system 300 may include at least one x-ray radiation source and corresponding detector array, similar to x-ray radiation source 104 and detector array 108 described above with reference to FIGS. 1-2.

CT imaging system 300 further includes a laser alignment system 305, similar to the laser alignment systems described above with reference to FIGS. 1-2. In the example shown by FIG. 3, laser alignment system 305 includes a plurality of laser radiation sources (e.g., laser diodes) mounted within an interior of a housing 303 of the gantry 301 of the CT imaging system 300 (e.g., mounted within gantry 301). For example, each of the laser radiation sources may be fixedly coupled to one or more mounting plates positioned within the interior of the housing 303, with the mounting plates encircling opening 322 of the gantry 301 within the interior. In some examples, one or more of the laser radiation sources may be fixedly coupled to the one or more mounting plates via an additional bracket or mounting device (e.g., in order to reinforce the coupling between the laser radiation sources and the mounting plates). Laser alignment system. 305 includes six laser radiation sources, similar to the example shown by FIG. 2. Specifically, laser alignment system 305 includes first laser radiation source 302, second laser radiation source 304, third laser radiation source 306, fourth laser radiation source 308, fifth laser radiation source 310, and a sixth laser radiation source (not shown) positioned opposite to first laser radiation source 302 across central axis 316 of the CT imaging system 300 (e.g., similar to the example shown by FIG. 2 and described above). In other examples, laser alignment system 305 may include a different number of laser radiation sources four, five, etc.). Each of the laser radiation sources of the laser alignment system 305 is mounted to the CT imaging system 300 via a corresponding laser mount, similar to the laser mount described below with reference to FIGS. 4-9.

In order to aid with positioning the subject 312 at the desired location within the imaging area of the CT imaging system 300 (e.g., centering the subject 312 within the opening 322, such that a center 314 of the portion of the subject 312 to be imaged is intersected by the beam of x-rays produced by the x-ray radiation source of the CT imaging system 300), the laser radiation sources of the laser alignment system 305 produce beams of visible light (e.g., red light, such as light having a wavelength of approximately 625 nanometers) which may indicate the position of the subject 312 relative to the beam of x-rays produced by the x-ray radiation source. In some examples, each beam of visible light produced by the laser radiation sources may project into the opening 322 through a respective aperture of the gantry 301.

The beam of x-rays produced by the x-ray radiation source of the CT imaging system 300 may be configured to intersect with central axis 316 of the CT imaging system 300 during conditions in which the CT imaging system 300 performs a scan of subject 312. In order to image the desired portion of subject 312, an operator of the CT imaging system 300 (e.g., a radiologist) may adjust the position of the subject 312 within the opening 322 and position the center 314 of the portion of subject 312 to be imaged at the location at which the beam of x-rays intersects with the central axis 316 (e.g., the axis of rotation of gantry 301, similar to center of rotation 206 described above with reference to FIG. 2). Because the wavelength of the x-rays produced by the x-ray radiation source is outside of the visible light spectrum (and further, because the x-ray radiation source may not be energized to produce the beam of x-rays during positioning of the subject 312 within the opening 322 in order to reduce an amount of exposure of the subject 312 to the beam of x-rays prior to imaging of the subject 312), the beams of visible light produced by the lasers of the laser alignment system 305 may provide visible indicators to the operator of the CT imaging system 300 in order to aid with positioning the center 314 of the portion of subject 312 to be imaged at the location at which the beam of x-rays intersects with the central axis 316.

For example, first laser 302 may be configured to produce a first light projection 320, second laser 304 and fifth laser 310 may be configured to produce a second light projection 317, third laser 306 and fourth laser 308 may be configured to produce a third light projection 318, and the sixth laser may be configured to produce a fourth light projection (not shown) positioned opposite to the first light projection 320 across central axis 316. During conditions in which the subject 312 is positioned within the opening 322, the first light projection 320, second light projection 317, third light projection 318, and fourth light projection may each illuminate portions of the subject 312 in order to indicate the position of the subject 312 relative to the intersection of the beam of x-rays with the central axis 316. Specifically, the first light projection 320 and fourth light projection illuminate opposing sides of the subject 312 in order to indicate the position of the subject 312 relative to the central axis 316 in the direction of the z-axis of reference axes 399 (e.g., the vertical direction of the CT imaging system 300 relative to a ground surface on which the CT imaging system 300 sits). The second light projection 317 illuminates a top end of the subject 312 in order to indicate the position of the subject 312 relative to the central axis 316 in the direction of the y-axis of reference axes 399. The third light projection 318 illuminates the top end of the subject 312 in a direction perpendicular to the second light projection 317 in order to indicate the position of the subject 312 relative to the central axis 316 in the direction of the x-axis of reference axes 399 (with the x-axis being perpendicular to the y-axis). For example, each of the first light projection 320, second light projection 317, third light projection 318, and fourth light projection may be a line of laser light projected onto the subject 312, as shown by FIG. 3. In other examples, the first light projection 320, second light projection 317, third light projection 318, and/or fourth light projection may be shaped differently (e.g., may be shaped as dots, crosshairs, etc.).

The position of each of the first light projection 320, second light projection 317, third light projection 318, and fourth light projection may be adjusted by adjusting the position of the corresponding lasers of the laser alignment system 305. For example, during assembly and/or maintenance of the CT imaging system 300 (e.g., conditions in which a portion of the housing 303 of the CT imaging system 300 is moved and/or removed in order to enable access to components housed within the interior of the housing 303), the position of one or more of the lasers of the laser alignment system 305 (e.g., first laser 302, second laser 304, third laser 306, fourth laser 308, fifth laser 310, and/or the sixth laser) may be adjusted (e.g., rotated or otherwise moved) via adjustment of the corresponding laser mounts of the lasers. As one example, the position of the first light projection 320 may be adjusted by adjusting the position of the first laser 302 relative to the gantry 301. In order to adjust the position of the first laser 302 relative to the gantry 301, one or more components of the laser mount coupling the first laser 302 to the gantry 301 may be rotated or otherwise moved. For example, the laser mount coupling the first laser 302 to the gantry 301 may include elements that enable the first laser 302 to rotate and translate relative to the gantry 301, similar to the laser mount described below with reference to FIGS. 4-9. Adjusting the position of the first laser 302 via the laser mount coupling the first laser 302 to the gantry 301 may adjust the position of the first light projection 320. In this way, the position of the first light projection 320 may be adjusted such that the vertical position of first light projection 320 (e.g., the position of the first light projection 320 in the direction of the z-axis of reference axes 399) is aligned with the vertical position of the central axis 316.

Although the first laser 302 and first light projection 320 are described above as an example, the second laser 304, third laser 306, fourth laser 308, fifth laser 310, and/or sixth laser may be adjusted in a similar way (e.g., via adjustment of a respective laser mount coupled to each corresponding laser) in order to adjust the position of the corresponding light projection (e.g., the second light projection 317, third light projection 318, and/or fourth light projection). For example, in order to adjust the position of the second light projection 317 (e.g., to align the second light projection 317 with the central axis 316 in the direction of the x-axis of reference axes 399), the position of second laser 304 may be adjusted via adjustment of the laser mount coupling the second laser 304 to the gantry 301 and/or the position of the fifth laser 310 may be adjusted via adjustment of the laser mount coupling the fifth laser 310 to the gantry 301. The position of the third light projection 318 may be adjusted in a similar way (e.g., via adjustment of the laser mount coupling the third laser 306 to the gantry 301 and/or adjustment of the laser mount coupling the fourth laser 308 to the gantry 301). Additionally, the position of the fourth light projection may be adjusted in a similar way (e.g., adjustment of the laser mount coupling the sixth laser to the gantry 301). Each of the laser mounts described above may be similar to the laser mount described below with reference to FIGS. 4-9.

Figure 4:
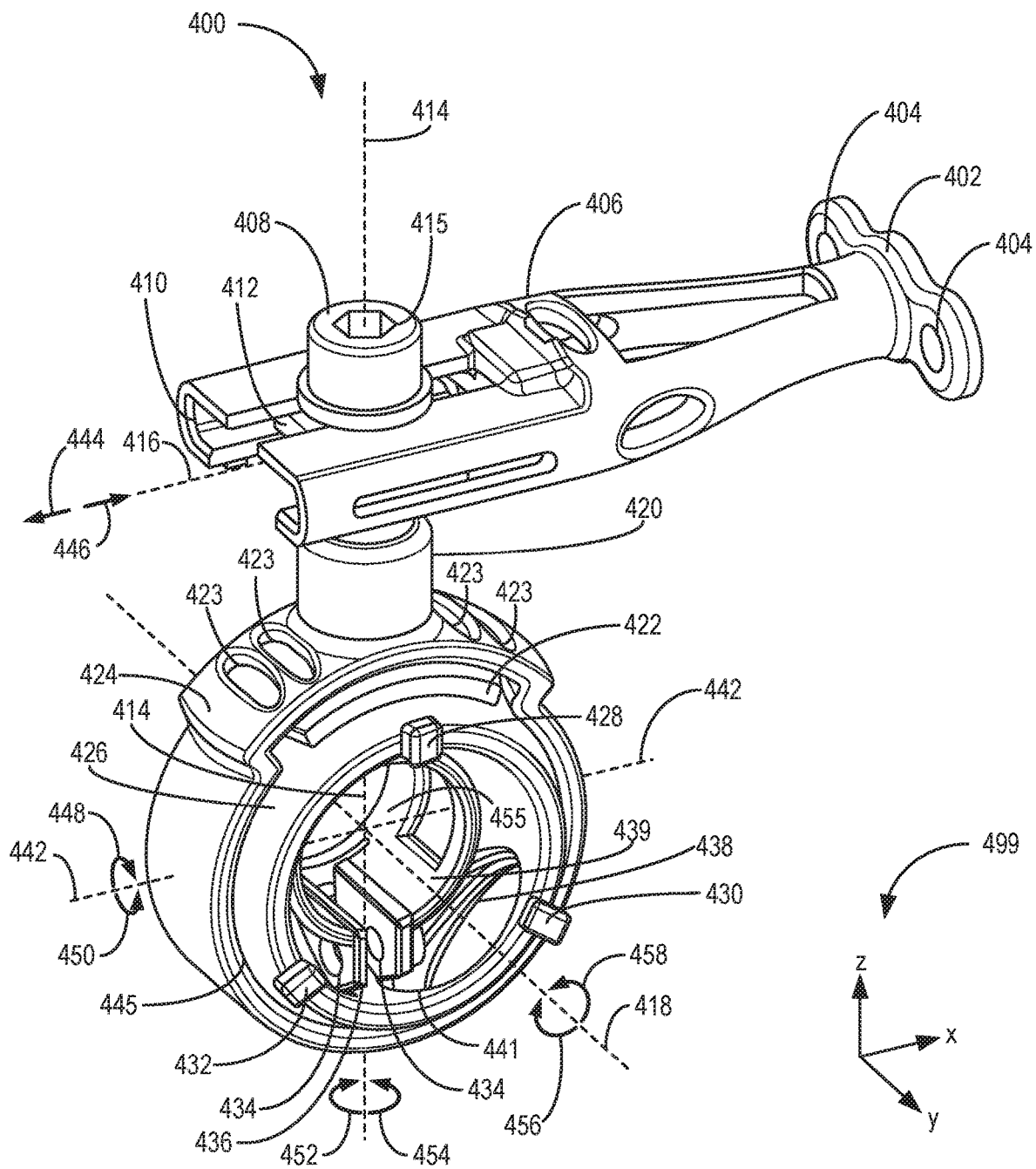
FIG. 4 shows a perspective view of a laser mount of a laser alignment system.

FIG. 4 shows a perspective view of a laser mount 400 (which may be referred to herein as a mount) which may be included within an imaging system, such as the CT system 100, imaging system 200, and/or CT imaging system 300 described above, which may each be referred to herein as medical imaging systems. Similar to the examples described above, laser mount 400 may be included by a laser alignment system of the imaging system (e.g., laser alignment system 305 described above with reference to FIG. 3) and may couple a corresponding laser radiation source (e.g., laser diode) to the imaging system. For example, laser mount 400 may be positioned within an interior of a gantry of the imaging system (e.g., similar to gantry 102 or gantry 301 described above), and the position of one or more components of the laser mount 400 may be adjusted in order to adjust the position of the laser and the position of the corresponding beam of visible light produced by the laser. In one example, each laser mount of the first laser 302, second laser 304, third laser 306, fourth laser 308, fifth laser 310, and sixth laser described above with reference to FIG. 3 may be similar to the laser mount 400.

Laser mount 400 includes an arm 406 (which may be referred to herein as a first section of the laser mount 400) adapted to fixedly couple the laser mount 400 to the imaging system (e.g., to the gantry of the imaging system) via bracket 402. As referred to herein, fixedly coupling the arm 406 to the gantry via the bracket 402 describes coupling the arm 406 to the gantry in such a way that the arm 406 is not moveable relative to the gantry. Specifically, the arm 406 may not move (e.g., rotate and/or translate) relative to the gantry during conditions in which the arm 406 is fixedly coupled to the gantry by the bracket 402. Bracket 402 includes openings 404 (e.g., holes), with each opening 404 adapted to receive a fastener (e.g., a bolt). Fasteners may be inserted through the openings 404 and through corresponding openings of the imaging system in order to fixedly couple the laser mount 400 to the imaging system.

The arm 406 includes a slot 410 adapted to receive a slideable element 412 of the laser mount 400. Slideable element 412 may be seated within the slot 410, and the position of the slideable element 412 relative to the arm 406 may be adjusted by sliding the slideable element 412 within the slot 410 along axis 416. For example, the slideable element 412 may move in a first direction 444 along axis 416 in order to move away from bracket 402. Slideable element 412 may additionally move in an opposing, second direction 446 along axis 416 in order to move toward bracket 402. Movement of the slideable element 412 in the first direction 444 and second direction 446 may be referred to herein as movement (e.g., translational movement) with one degree of freedom. For example, movement of the slideable element 412 within the slot 410 with the one degree of freedom does not include moving the slideable element 412 in directions other than the first direction 444 and second direction 446, and does not include rotation of the slideable element 412 within the slot 410.

The position of the slideable element 412 within the slot 410 may be locked via a lock mechanism including a first lock element 408 and a second lock element 422. The first lock element 408 and second lock element 422 may be referred to herein collectively as the lock mechanism of the laser mount 400. In one example, the first lock element 408 may be a fastener (e.g., a bolt) including a shank 413 (shown by FIG. 5) inserted through each of the slot 410 and the slideable element 412. For example, the slideable element 412 may include a passage 411 (shown by FIGS. 5, 6, and 8-9) adapted to receive the shank 413 of the first lock element 408. In one example, the passage 411 may include counterpart threads adapted to engage with threads of the shank 413 of the first lock element 408. As the first lock element 408 is tightened against the arm 406 by further engaging the threads of the first lock element 408 with the counterpart threads of the passage of the slideable element 412 and engaging the first lock element 408 with the second lock element 422 as described below, the lock mechanism may lock the slideable element 412 to the slot 410 such that the slideable element 412 does not move (e.g., slide) within the slot 410.

The engagement of the first lock element 408 with the second lock element 422 may maintain a position of the first lock element 408 relative to the slideable element 412, such that during conditions in which the position of the slideable element 412 is locked by the lock mechanism, the engagement of the first lock element 408 with the second lock element 422 maintains the lock mechanism in the locked configuration. As the first lock element 408 is loosened from the arm 406 by disengaging the threads of the first lock element 408 with the counterpart threads of the passage of the slideable element 412 and disengaging the first lock element 408 from the second lock element 422, the slideable element 412 may be unlocked such that the slideable element 412 is able to slide within the slot 410 along axis 416. The locking and unlocking of the slideable element 412 is described in further detail below with reference to FIGS. 8-9.

The first lock element 408 may be tightened against the arm 406 via a single input of the lock mechanism (e.g., head 415 of first lock element 408) in order to adjust the engagement of the first lock element 408 with the second lock element 422. For example, the head 415 may be rotated in a first direction in order to drive the first lock element 408 against the second lock element 422 to adjust the lock mechanism from the unlocked configuration to the locked configuration (e.g., adjust the slideable element 412 from a condition in which the slideable element 412 is free to slide within the slot 410 in the direction 444 or direction 446, to a condition in which the position of the slideable element 412 is locked within the slot 410). Further, the head 415 may be rotated in a second direction opposite to the first direction in order to drive the first lock element 408 away from the second lock element 422 to adjust the lock mechanism from the locked configuration to the unlocked configuration (e.g., adjust the slideable element 412 from the condition in which the position of the slideable element 412 is locked within the slot 410, to the condition in which the slideable element 412 is free to slide within the slot 410 in the direction 444 or direction 446). In this way, the position of the slideable element 412 may be locked or unlocked relative to the slot 410 via the single input of the lock mechanism. Further, locking the position of the slideable element 412 via the single input may additionally lock a position of inner housing 426 relative to outer housing 424, and unlocking the position of the slideable element 412 relative to the slot 410 as described above via the single input may additionally unlock a position of the inner housing 426 relative to the outer housing 424, as described further below.

Slideable element 412 is joined to outer housing 424 of the laser mount 400 by extension 420. In one example, each of the slideable element 412, outer housing 424, and extension 420 is formed together as a single, continuous piece (e.g., a single unit). The slideable element 412, outer housing 424, and extension 420 may be referred to herein collectively as a second section of the laser mount 400. In each example, the slideable element 412, outer housing 424, and extension 420 are not moveable relative to each other. For example, as the slideable element 412 moves (e.g., slides) within the slot 410 as described above in the first direction 444, the outer housing 424 and extension 420 similarly move in the first direction 444 due to the outer housing 424, slideable element 412, and extension 420 being fixedly joined to each other. By adjusting the position of the slideable element 412 within the slot 410, the position of the extension 420 and the outer housing 424 is similarly adjusted.

The laser mount 400 further includes an inner housing 426 disposed (e.g., seated) within the outer housing 424. The inner housing 426 may be referred to herein as a third section of the laser mount 400. Inner housing 426 is seated within the outer housing 424 and is rotatable relative to the outer housing 424 during conditions in which the laser mount 400 is in an unlocked condition, as described further below. However, during conditions in which the laser mount 400 is in a locked condition (e.g., a condition in which second lock element 422 presses against the inner housing 426, as described further below), the inner housing 426 is not rotatable relative to the outer housing 424.

During conditions in which the laser mount 400 is in the unlocked condition, the inner housing 426 is rotatable within the outer housing 424 with three degrees of freedom (e.g., three mutually orthogonal rotational degrees of freedom). Specifically, the inner housing 426 may rotate with a first degree of freedom in a first direction 456 and an opposing, second direction 458 around axis 418, the inner housing 426 may rotate with a second degree of freedom in a third direction 448 and an opposing, fourth direction 450 around axis 442, and the inner housing 426 may rotate with a third degree of freedom in a fifth direction 452 and an opposing, sixth direction 454 around axis 414, with the axes 418, 442, and 414 being mutually perpendicular (e.g., orthogonal) to each other (e.g., axis 418 is positioned parallel with the y-axis of reference axes 499, axis 442 is positioned parallel with the x-axis of reference axes 499, and axis 414 is positioned parallel with the z-axis of reference axes 499). The inner housing 426 further includes a plurality of protrusions (e.g., first protrusion 428, second protrusion 430, and third protrusion 432) configured to reduce a likelihood that the inner housing 426 is rotated outside of a predetermined range of rotation.

As one example, prior to rotating the inner housing 426, the inner housing 426 may be in the initial position shown by FIG. 4 (e.g., corresponding to 0 degrees of rotation around the axes 418, 442, and 414). The first protrusion 428, second protrusion 430, and third protrusion 432 may be positioned such that the inner housing 426 may be rotated in the direction 452 by 10 degrees relative to the initial position shown by FIG. 4, at which point the third protrusion 432 engages with the outer housing 424 (e.g., presses against the outer housing 424) and prevents further rotation of the inner housing 426 in the direction 452 (e.g., prevents the inner housing 426 from being rotated in the direction 452 by more than 10 degrees relative to the initial position). Similarly, from the initial position, the inner housing 426 may be rotated by 10 degrees in the direction 448, at which point the second protrusion 430 and third protrusion 432 engage with the outer housing 424 and prevent further rotation of the inner housing 426 in the direction 448. However, in some examples, rotating the inner housing 426 in either of the direction 458 or direction 456 may not engage the first protrusion 428, second protrusion 430, or the third protrusion 432 with the outer housing 424. As a result, range of rotation of the inner housing 426 in the direction 458 or the direction 456 may be 360 degrees. Although the range of rotation of the inner housing 426 from the initial position around the axes 414 and 442 is described as 10 degrees above, in other examples, the range of rotation may be a different amount (e.g., 5 degrees, 15 degrees, etc.).

By enabling the inner housing 426 to rotate relative to the outer housing 424 as described above, and by enabling the slideable element 412 to move within the slot 410 as described above, the inner housing 426 is movable with four degrees of freedom (e.g., three rotational degrees of freedom corresponding to rotation around axes 418, 442, and 414, and one translational degree of freedom corresponding to translation in direction 444 and opposing direction 446).

The inner housing 426 includes an annular section 439 shaped to couple with a laser radiation source (e.g., laser diode). The annular section 439 forms a clamp 436 having openings 434, with the openings 434 adapted to receive a fastener (e.g., a bolt). Further, outer housing 424 includes at least one opening 438 extending through a thickness 429 of the outer housing 424 in a radial direction of the outer housing 424 (along radial axis 443 extending radially relative to a center of a through-hole of the outer housing 424 adapted house and encircle the inner housing 426, for example) configured to enable the fastener to be more easily inserted through each of the openings 434. Similarly, inner housing 426 includes at least one opening 441 extending through a thickness 427 of the inner housing 426 in a radial direction of the inner housing 426 (along radial axis 443 extending radially relative to a center of rotation of the inner housing 426 corresponding to an intersection of axes 442, 418, and 414, for example) configured to align with a corresponding opening 438 of the outer housing 424. The opening 438 may radially align with the opening 441 (e.g., axis 443 may be coaxial with axis 447) such that the fastener may be inserted through each of the opening 438 and the opening 441.

For example, a threaded fastener may be inserted through opening 438 of the outer housing 424 and coupled to the clamp 436 of the annular section 439 of the inner housing 426 at each of the openings 434. In one example, the fastener may be fastened to the clamp 436 by a nut having counterpart threads adapted to engage with the threads of the fastener. By tightening the threads of the nut against the threads of the fastener (e.g., further engaging the threads of the nut with the threads of the fastener), the clamp 436 and annular section 439 may be compressed around the laser in order to maintain the position of the laser radiation source relative to the inner housing 426 (e.g., fixedly couple the laser radiation source with the inner housing 426). For example, an inner surface 455 of the annular section 439 may be compressed against outer surfaces of the laser radiation source via compression of the clamp 436 by the fastener inserted through the openings 434 in order to lock the laser to the annular section 439. The fastener may apply force to opposing sides of the clamp 436 (e.g., at the opposing openings 434) in order to press the inner surface 455 against the outer surfaces of the laser radiation source.

An example of a laser 600 coupled with the annular section 439 is shown by FIG. 6 and described further below.

During conditions in which the laser is coupled to the annular section 439 as described above, adjusting the position of the inner housing 426 by rotating the inner housing 426 within the outer housing 424 and/or moving the inner housing 426 by moving the slideable element 412 within the slot 410, the position of the laser is similarly adjusted. As one example, because the laser is fixedly coupled to the annular section 439 of the inner housing 426, rotating the inner housing 426 in the direction 456 similarly rotates the laser in the direction 456 by the same amount. As another example, moving the slideable element 412 within the slot 410 in the direction 444 similarly moves the outer housing 424 and inner housing 426 in the direction 444 by the same amount, and because the laser is fixedly coupled to the inner housing 426, the laser is similarly moved in the direction 444 by the same amount. In this way, the laser is movable with four degrees of freedom (e.g., the same four degrees of freedom through which the inner housing 426 is movable, as described above). By configuring the laser to be movable via the laser mount 400 in this way, an operator of the imaging system may more easily adjust the position of the laser (e.g., in order to adjust the position of a beam of visible light produced by the laser, similar to the example described above with reference to FIG. 3).

Turning now to FIG. 5, a cross-sectional view of the laser mount 400 is shown. The view shown by FIG. 5 is along a cross-sectional plane defined by the z-axis and x-axis of the reference axes 499 of FIG. 4. FIG. 5 illustrates clearances between the inner housing 426, the outer housing 424, and the second lock element 422 via first inset 500 and second inset 502.

Second lock element 422 is configured to lock the rotation of the inner housing 426 relative to the outer housing 424 during conditions in which the laser mount 400 is in the locked configuration. Second lock element 422 is shaped to surround a portion of the inner housing 426 at a location opposite to the clamp 436. During conditions in which the laser mount 400 is in the unlocked configuration (e.g., the configuration in which the second lock element 422 does not lock the rotation of the inner housing 426 relative to the outer housing 424), the second lock element 422 is separated from the inner housing 426 by a clearance 504 (e.g., a gap), as shown by the enlarged view of first inset 500. However, during conditions in which the laser mount 400 is in the locked configuration (e.g., the configuration in which the second lock element 422 locks the rotation of the inner housing 426 relative to the outer housing 424), the clearance 504 is decreased such that the second lock element 422 engages in direct, face-sharing contact with the inner housing 426. Face-sharing contact between the second lock element 422 and the inner housing 426 as described herein refers to the surfaces of the second lock element 422 directly contacting the surfaces of the inner housing 426, with no other components positioned between the surfaces of the second lock element 422 and the surfaces of the inner housing 426. The locked and unlocked configurations are described further below with reference to FIGS. 8-9.

Further, a clearance 506 is formed between the second lock element 422 and the outer housing 424. In some examples, during conditions in which the laser mount 400 is in the locked configuration, the clearance 506 may be reduced relative to conditions in which the laser mount 400 is in the unlocked condition.

As shown by the enlarged view of second inset 502, a clearance 508 is formed between the inner housing 426 and the outer housing 424. Clearance 508 may extend around an entire outer surface of the inner housing 426, such that the inner housing 426 is separated from the outer housing 424 by the clearance 508 at each location along the entire outer surface of the inner housing 426. The clearance 508 enables the inner housing 426 to rotate relative to the outer housing 424 without the outer housing 424 interfering with the motion of the inner housing 426. As described further below, in some examples, the laser mount 400 and its components (e.g., the inner housing 426, outer housing 424, second lock element 422, etc.) may be formed via an additive manufacturing process (e.g., 3D printing). Forming the laser mount 400 and its components in this way may enable the size of the clearances to be reduced (e.g., reduce the size of clearances 506, 504, and/or 508) and may increase a reliability of the operation of the laser mount 400 (e.g., decrease a likelihood of undesirable interference between components of the laser mount 400).

FIG. 6 shows another cross-sectional view of the laser mount 400. The cross-sectional plane of FIG. 6 is defined by the z-axis and y-axis of reference axes 499 of FIG. 4. In the view shown by FIG. 6, a laser radiation source 600 (e.g., laser diode) is coupled to the inner housing 426 of the laser mount 400, as described above. Specifically, the laser 600 is coupled to the inner housing 426 via clamp 436 as described above, such that adjusting the position of the inner housing 426 (e.g., rotating the inner housing 426 within the outer housing 424) similarly adjusts the position of the laser 600. The laser 600 may be electronically coupled to the imaging system via one or more electrical connections (e.g., wires, such as electrical connector 602). Arrow 604 indicates a direction of a beam of visible light emitted by the laser 600. By rotating the inner housing 426 within the outer housing 424, the laser 600 is similarly rotated and the direction of arrow 604 is similarly rotated. For example, rotating the inner housing 426 in the direction 454 shown by FIG. 4 similarly rotates the laser 600 in the direction 454 by a same amount. As a result, the direction of the beam of visible light produced by the laser and indicated by arrow 604 is similarly rotated in the direction 454. Adjusting the position of the inner housing 426 during conditions in which the laser 600 is coupled to the inner housing 426 may similarly adjust the position of the beam of visible light produced by the laser 600. In this way, the operator of the imaging system may adjust the position of the beam of visible light produced by the laser 600 in order to aid with imaging of the subject, similar to the examples described above (e.g., with reference to FIG. 3).

Although the laser mount 400 is described herein as coupleable with a laser radiation source, in other examples the laser mount 400 may couple with a different type of component relative to laser 600. For example, the inner housing 426 may couple with a sensor (e.g., light sensor, acoustic sensor, etc.) via clamp 436 in order to enable a position of the sensor to be adjusted in a similar way relative to the adjustment of the laser 600 as described above.

FIG. 7 shows an enlarged view of a lower portion of the laser mount 400. Specifically, FIG. 7 shows an enlarged view of opening 438, described above with reference to FIG. 4. The opening 438 is formed in the outer housing 424 and enables the clamp 436 to be more easily accessed (e.g., in order to couple and/or decouple the laser 600, shown by FIG. 6, to/from the inner housing 426). For example, as described above, a fastener may be inserted through the opening 438 and into the openings 434 of the inner housing 426 in order to compress the clamp 436 and maintain the coupled position of the laser 600 relative to the inner housing 426.

Turning now to FIGS. 8-9, cross-sectional views of the laser mount 400 are shown, similar to the cross-sectional view shown by FIG. 5. FIG. 8 shows the laser mount 400 in the unlocked configuration described above, and FIG. 9 shows the laser mount 400 in the locked configuration described above.

As shown by FIGS. 8-9, the slideable element 412 includes a first end 806 and a second end 808, with the first end 806 positioned further from the bracket 402 (shown by FIGS. 3-4) than the second end 808 during conditions in which the slideable element 412 is seated within the slot 410 of the arm 406. The slideable element 412 includes a plurality of notches 804 configured to increase a flexibility of the slideable element 412. In the example shown by FIGS. 8-9, the slideable element 412 includes two notches positioned at opposing sides of the slideable element 412. However, in other examples, the slideable element 412 may include a different number of notches (e.g. three, four, etc.).

During conditions in which the laser mount 400 is in the unlocked configuration, the slideable element 412 is seated within the slot 410 such that a clearance 802 (e.g., a gap) is formed between the slideable element 412 and a top, inner surface 803 of the arm 406 forming the slot 410. The clearance 802 enables the slideable element 412 to move within the slot 410 as described above (e.g., slide along axis 416). By moving the slideable element 412 within the slot 410, the position of the inner housing 426 and outer housing 424 relative to the arm 406 may be adjusted. Because the arm 406 may be fixedly coupled to the imaging system (e.g., coupled to the gantry of the imaging system), moving the slideable element 412 within the slot 410 adjusts the position of the inner housing 426 and outer housing 424 relative to the imaging system. In this way, a position of a laser coupled to the inner housing 426 (e.g., laser 600 shown by FIG. 6 and described above) may be similarly adjusted by adjusting the position of the inner housing 426 and outer housing 424 via the slideable element 412.

As shown by inset 800, during conditions in which the laser mount 400 is in the unlocked configuration, a clearance 811 (e.g., a gap) is formed between an end surface 610 (e.g., terminal surface or terminal end) of the second lock element 422 and an end surface 608 (e.g., terminal surface or terminal end) of the first lock element 408 (e.g., end surface 608 of shank 413 of the first lock element 408) inserted through the slideable element 412. In this configuration, the end surface 608 of the first lock element 408 may not be in direct face-sharing contact with the end surface 610 of the second lock element 422. As a result, the second lock element 422 is not pressed into engagement with the inner housing 426 and does not lock the rotation of the inner housing 426.

However, during conditions in which the laser mount 400 is in the locked configuration as shown by FIG. 9, the end surface 608 of the first lock element 408 is pressed against the end surface 610 of the second lock element 422. Pressing the end surface 608 of the first lock element 408 against the end surface 610 of the second lock element 422 as shown by inset 900 closes the clearance 811 between the end surface 608 and the end surface 610 and presses surfaces of the second lock element 422 against surfaces of the inner housing 426. By pressing the second lock element 422 against the inner housing 426 in this way, the surfaces of the second lock element 422 interfere with the surfaces of the inner housing 426 and lock the position of the inner housing 426 relative to the outer housing 424.

In order to adjust the laser mount 400 from the unlocked configuration shown by FIG. 8 to the locked configuration shown by FIG. 9, the first lock element 408 is tightened against the arm 406. For example, as described above, the first lock element 408 may include threads adapted to engage with counterpart threads of the passage of the slideable element 412. In the unlocked configuration, the threads of the first lock element 408 may not be fully engaged with the counterpart threads of the passage of the slideable element 412 (e.g., each thread of the first lock element 408 may not be engaged with a corresponding counterpart thread of the passage). However, the first lock element 408 may be rotated around axis 414 (e.g., by a tool) in order to increase the engagement of the threads of the first lock element 408 with the counterpart threads of the passage. By increasing the engagement of the threads of the first lock element 408 with the counterpart threads of the passage, the first lock element 408 may be driven in the direction of the second lock element 422 in order to press the end surface 608 of the first lock element 408 against the end surface 610 of the second lock element 422.

As described above, pressing the end surface 608 of the first lock element 408 against the end surface 610 of the second lock element 422 (e.g., by driving the first lock element 408 toward the second lock element 422) causes the second lock element 422 to press against the inner housing 426 in order to lock the movement of the inner housing 426 relative to the outer housing 424.

However, driving the first lock element 408 toward the second lock element 422 additionally drives the slideable element 412 away from the second lock element 422 and presses the slideable element 412 against the top, inner surface 803 of the arm 406 forming the slot 410. In this way, the movement of the inner housing 426 relative to the outer housing 424 and the movement of the slideable element 412 relative to the slot 410 and arm 406 may be locked or unlocked together via the single input of the locking mechanism (e.g., head 415 of the first lock element 408). Specifically, as the slideable element 412 is driven away from the second lock element 422 due to the engagement of the first lock element 408 with the passage of the slideable element 412, the first end 806 and second end 808 of the slideable element 412 may temporarily bend (e.g., curve) slightly at the notches 804. For example, the first end 806 may bend at the notch 804 positioned at the first end 806, and the second end 808 may bend at the notch 804 positioned at the second end 808. The bending of the first end 806 and second end 808 may increase the amount by which the first lock element 408 is able to be driven toward the second lock element 422 and may increase the amount of force applied to the second lock element 422 by the first lock element 408 as well as the amount of force applied to the inner surface 803 of the arm 406 by the slideable element 412. The increased amount of force applied to the second lock element 422 by the first lock element 408 may increase a locking strength of the second lock element 422 against the inner housing 426. Additionally, pressing the slideable element 412 against the top, inner surface 803 of the arm 406 via the first lock element 408 locks the position of the slideable element 412 within the slot 410. Increasing the amount of force applied to the inner surface 803 of the arm 406 by the slideable element 412 as described above may increase a locking strength of the slideable element 412 against the inner surface 803.

In the configuration described above, the position of the inner housing 426 relative to the arm 406 is lockable via the first lock element 408 without additional fasteners. Further, because the laser (e.g., laser 600) may be coupled to the inner housing 426 and the position of the laser may be adjusted via adjustment of the position of the inner housing 426 as described above, the position of the laser relative to the arm 406 is lockable via the first lock element 408 without additional fasteners.

As one example of operating the laser mount 400, the laser mount 400 may be coupled to the gantry of the imaging system via the bracket 402 (shown by FIGS. 4-5). The laser 600 (shown by FIG. 6) may be coupled to the inner housing 426 via the clamp 436, such that the rotation of the laser 600 is locked to the rotation of the inner housing 426. The first lock element 408 may be loosened (e.g., not fully engaged with the passage of the slideable element 412) such that the second lock element 422 is not pressed against the inner housing 426 by the first lock element 408, and the slideable element 412 is not pressed against the inner surface 803. The operator may adjust the position of the laser 600 by adjusting the position of the inner housing 426 until the beam of visible light produced by the laser 600 is directed toward the desired target (e.g., the location at which the beam of x-rays produced by the x-ray radiation source of the imaging system intercepts the center of rotation of the imaging system). For example, the operator may rotate the inner housing 426 within the outer housing 424 and/or slide the slideable element 412 within the slot 410 in order to adjust the position of the inner housing 426 and laser 600 relative to the arm 406 and gantry of the imaging system. The operator may then adjust the laser mount from the unlocked configuration to the locked configuration by tightening the first lock element 408 against the arm 406 (e.g., further engaging the threads of the first lock element 408 with the counterpart threads of the passage of the slideable element 412). Tightening the first lock element 408 against the arm 406 engages the second lock element 422 with the inner housing 426 to lock the rotation of the inner housing 426 relative to the outer housing 424. Additionally, tightening the first lock element 408 against the arm 406 presses the slideable element 412 against the top, inner surface 803 of the arm 406 to lock the position of the slideable element 412 relative to the arm 406 and the gantry of the imaging system. In this way, in the unlocked configuration, the position of the laser 600 may be adjusted with four degrees of freedom (e.g., three rotational degrees of freedom around axes 414, 418, and 442 as shown by FIG. 4, and one translational degree of freedom in directions 444 and 446 as shown by FIG. 4), and by adjusting the laser mount 400 from the unlocked configuration to the locked configuration via tightening the single first lock element 408 against the arm 406, the position of the laser 600 may be locked with respect to all four degrees of freedom (e.g., the laser 600 is locked from rotating around axes 414, 418, and 442, and is further locked from translating in directions 444 and 446).

As described above, in some examples, the slideable element 412, outer housing 424, and extension 420 may be formed together as a single, continuous piece (e.g., a single unit). In one example, the slideable element 412, outer housing 424, and extension 420 may be formed together from a same material via an additive manufacturing process (e.g., 3D printing). Similarly, the inner housing 426 and its components (e.g., clamp 436, protrusions 428, 430, and 432, etc.) may be formed together via the additive manufacturing process. The arm 406 may additionally be formed via the additive manufacturing process as a separate piece relative to the inner housing 426 and outer housing 424.

Each component of the laser mount 400 may be manufactured at least in part using an additive manufacturing process such as 3D printing. By utilizing additive manufacturing, the inner housing 426 may be seated within the outer housing 424 during manufacturing in a fast and low-cost manner, without utilizing multiple individual structures that are welded or otherwise fastened together. Further, changes to the geometry of the laser mount, such as changes in a diameter of the inner housing 426 and/or outer housing 424, as well as changes to the overall dimensions of the laser mount, may be made by adjusting the model of the laser mount used as instructions for the additive manufacturing, and without utilizing completely different manufacturing equipment. Thus, a variety of different laser mounts may be manufactured for different sized lasers or imaging system gantries and/or for different desired properties at a large scale and low cost.

FIG. 10 is a flow chart illustrating an example method 1000 for manufacturing a laser mount configured to be housed in a vaporizing chamber of an anesthetic vaporizer system, such as laser mount 400 of FIG. 4. Method 1000 may be carried out at least in part by a 3D printing device, which may be operatively/communicatively coupled to a printer-interfacing computing device.

At 1002, method 1000 includes obtaining or generating a 3D model of the laser mount. The model of the laser mount may be a computer aided design (CAD) file, additive manufacturing file (AMF), or other 3D modeling file. The 3D model of the laser mount may be generated on the printer-interfacing computing device. In some examples, the 3D model may be generated entirely from operator instructions via the CAD program. In other examples, the 3D model may be generated at least in part from information received from a 3D scanner (e.g., a laser scanner) that may image a physical model of the laser mount. The 3D model may define the dimensions of the laser mount, exterior and interior structures of the laser mount, and material properties of the laser mount, thereby fully representing, in a digital format, the final form of the laser mount that will be produced.

At 1004, a plurality of 2D slices of the 3D model of the laser mount are generated. The slices may be generated on the printer-interfacing computing device and then the plurality of slices are sent to the printing device as an STL file, or the 3D model of the laser mount may be sent to the printing device, and the printing device may slice the 3D model into the plurality of slices to generate an STL file. In doing so, the 3D model is sliced into hundreds or thousands of horizontal layers of a suitable thickness, such as horizontal layers having a thickness within a range of 20 microns to 100 microns. In other examples, the horizontal layers may have a different thickness (e.g., a thickness within a range of 40 microns to 120 microns, as one non-limiting example).

At 1006, the printing device prints the first slice on a build plate or other suitable base material. When the printing device prints from the STL file, the printing device creates or prints the laser mount layer-by-layer on the build plate. The printing device reads every slice (or 2D image) from the 3D model and proceeds to create the 3D laser mount by laying down (or printing) successive layers of material on an upper, planar surface of the build plate until the entire laser mount is created. Each of these layers can be seen as a thinly sliced horizontal cross section of the eventually completed or printed 3D laser mount.

The printing device may be a suitable device configured to print metal, such as aluminum, stainless steel, titanium, etc., or polymers, such as acrylonitrile butadiene styrene (ABS), nylon, polyetherimide, etc. In some examples, the printing device may utilize selective laser melting (SLM) technology, direct metal laser sintering (DMLS) technology, or other suitable metal printing technology.

During printing, the print head(s) is moved, in both horizontal and vertical directions, to complete or print each layer of the 3D model, by a controlled mechanism that is operated by control software running on the printing device, e.g., a computer-aided manufacturing (CAM) software package adapted for use with the printing device. The build plate is typically stationary with its upper planar surface parallel to a horizontal plane, although in some examples the build plate may be moved up and down vertically (i.e., in the z-direction). The printed material solidifies to form a layer (and to seal together layers of the 3D laser mount), and the print head or build plate is then moved vertically prior to starting the printing of the next layer. This process is repeated until all layers of the 3D laser mount have been printed.

Accordingly, at 1008, method 1000 includes sequentially printing each additional slice. At 1010, the printed laser mount is dried and/or cured. The drying/curing of the printed laser mount may be performed after each layer deposition, and/or the drying/curing may be performed after the entire laser mount is printed. If support structures are printed in the voids of the laser mount (e.g., scaffolding-like structures or perforated structures), the support structures may be removed manually and/or with a tool.

Thus, method 1000 provides for 3D printing of a laser mount adapted to be coupled to a gantry of a medical imaging system. Method 1000 is directed to printing the inner housing and outer housing of the laser mount and their components (e.g., extension 420, clamp 436, slideable element 412, etc.) together as a first unit, with the inner housing rotatable relative to the outer housing, and printing the arm and its components (e.g., slot 410, bracket 402, etc.) as a second unit separate from the first unit. As such, the 3D model of the laser mount may include multiple 3D models, each of a different section of the laser mount. For example, the laser mount may be divided into a plurality of sections, such as a first section that includes the inner housing and the outer housing, and a second section that includes the arm. Each section may be printed independently, and then the sections may be coupled together via a fastener (e.g., first lock element 408).

In still further examples, the laser mount may be manufactured using a mold. The mold may be generated by first 3D printing a model of the laser mount in a suitable material that may be solid at room temperature but changes to liquid at a relatively low temperature that is greater than room temperature, such as wax. A plaster mold may be formed over the wax model, and after the plaster dries, the wax may be melted and drained from the mold. The mold may then be filled with molten metal (e.g., steel, aluminum, titanium, etc.). Once the metal cools, the plaster may be removed to generate the laser mount.

Thus, the laser mount described above with respect to FIGS. 4-9 may be manufactured using additive manufacturing technology, such as 3D printing. In an example, the laser mount described herein may be manufactured according to a computer readable medium containing computer readable instructions which, when executed on a 3D printer, cause the printer to print the laser mount, where the laser mount comprises an inner housing disposed within an outer housing, with the inner housing rotatable relative to the outer housing. The laser mount further comprises a lock element separated from each of the inner housing and the outer housing by respective clearances In an example, a method of creating a computer readable 3D model suitable for use in additive manufacturing of a laser mount configured to be coupled (e.g., mounted) to a gantry of a medical imaging system is provided, wherein the laser mount comprises an outer housing, an inner housing disposed within the outer housing, a lock element positioned between the inner housing and the outer housing, a slideable element joined to an extension of the outer housing, and an arm having a slot adapted to receive the slideable element. In an example, the method includes obtaining specifications of the laser mount. The specifications may be obtained from user input (e.g., via a 3D modeling program such as CAD) and/or from information obtained from a 3D scanner. For example, the 3D scanner may image a physical model or prototype of the laser mount. The method further includes generating the computer readable 3D model of the laser mount based on the obtained specifications. The 3D model may be generated using CAD or another 3D modeling program. In some examples, the method further includes sending the 3D model to a printing device. The 3D model may be converted into an STL file or other suitable format readable by the printing device. The printing device may then print the laser mount according to the specifications set forth by the 3D model.

By manufacturing the laser mount via the additive manufacturing process as described above, the inner housing and lock element may be seated within the outer housing during manufacturing, and the clearances between the inner housing, outer housing, and lock element may be reduced. For example, by seating the inner housing and lock element within the outer housing during manufacturing via the additive manufacturing process (e.g., printing the inner housing and lock element within the outer housing while the inner housing, lock element, and outer housing are printed together from a single 3D model), the inner housing may be more precisely aligned with the outer housing (e.g., the clearance between the inner housing and outer housing may be reduced), and the lock element may be more precisely aligned with the inner housing (e.g., the clearance between the lock element and the inner housing may be reduced). As a result, an amount of force to engage the lock element with the inner housing may be reduced (e.g., the fastener driving the lock element toward the inner housing may be driven by a smaller amount to engage the lock element with the inner housing), and an ease of movement of the inner housing within the outer housing may be increased (e.g., a likelihood of the outer housing interfering with the rotation of the inner housing may be reduced).

FIGS. 4-9 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

By configuring the laser mount as described above, the position of the laser coupled to the laser mount may be more easily adjusted relative to the imaging system. The laser mount may be adjusted to the unlocked configuration or the locked configuration via adjustment of the single fastener coupled to the slideable element, which may increase an ease with which the position of the laser is locked and/or unlocked relative to the imaging system. In this way, the position of the laser may be adjusted with four degrees of freedom. By manufacturing the laser mount via the additive manufacturing process, the clearances between the various components of the laser mount may be reduced, and reliability may be increased. Further, manufacturing the laser mount via the additive manufacturing process may reduce a weight of the laser mount by enabling the laser mount to be manufactured with cutouts, undercuts, and other complex geometries. For example, the laser mount may be manufactured with a plurality of openings to reduce the weight of the laser mount, such as openings 423 shown by FIG. 4 and openings 425 shown by FIG. 5. As a result, because the laser mount is adapted to couple to the gantry of the imaging system, and because the laser mount may be manufactured with the reduced weight, the laser mount contributes less to the overall weight of the gantry of the imaging system, and the gantry may be rotated more easily (e.g., with less force) to perform a scan of a subject (e.g., a patient).

The technical effect of configuring the laser mount to include the inner housing and lock element disposed within the outer housing, with the outer housing joined to the slideable element via the extension, is to enable the position of the laser coupled to the inner housing to be adjusted with four degrees of freedom.

In one embodiment, a medical imaging system includes: a gantry; and a laser mount including a first section fixedly coupled to the gantry and a second section moveably coupled with the first section, the second section including an opening adapted to receive a laser radiation source, where the opening is movable with four degrees of freedom relative to the first section. In a first example of the medical imaging system, a position of the opening relative to the first section is lockable via a single input of a lock element. In a first example of the medical imaging system, the first section is a mounting arm.

In one embodiment, a medical imaging system comprises: a gantry; and a laser mount including: a first section fixedly coupled to the gantry; a second section seated within the first section and slideable within the first section; and a third section seated within the second section and rotatable within the second section, the third section adapted to house a laser radiation source. In a first example of the medical imaging system, the laser mount further comprises a lock element disposed between the second section and the third section with a terminal end of the lock element positioned within a passage of the second section, the lock element adapted to lock a position of the third section relative to the second section. A second example of the medical imaging system optionally includes the first example, and further includes wherein the laser mount is positioned within an interior of a housing of the gantry and is fixedly coupled to a mounting plate of the gantry within the housing. A third example of the medical imaging system optionally includes one or both of the first and second examples, and further includes wherein the third section is rotatable within the second section with three degrees of freedom. A fourth example of the medical imaging system optionally includes one or more or each of the first through third examples, and further includes wherein the second section is slideable within the first section with only one degree of freedom, in only a first direction and an opposing, second direction.

In one embodiment, a mount comprises: an outer housing coupled to an arm of the mount by a slideable element seated within a slot of the arm; an inner housing rotatably seated within the outer housing and separated from the outer housing by a first clearance; and a lock element disposed between the inner housing and outer housing and separated from the inner housing by a second clearance, the lock element including a first surface adapted to engage with an outer surface of the inner housing to lock a position of the inner housing relative to the outer housing. In a first example of the mount, the slideable element includes a first end and a second end adapted to engage with an inner surface of the arm to lock the outer housing to the arm. A second example of the mount optionally includes the first example, and further includes wherein the first end includes a first notch and the second end includes a second notch, and wherein the first end is adapted to bend at the first notch to engage the inner surface and the second end is adapted to bend at the second notch to engage the inner surface. A third example of the mount optionally includes one or both of the first and second examples, and further includes wherein the lock element includes a terminal end positioned opposite to the first surface and disposed within a passage of the outer housing, the passage adapted to receive a shank. A fourth example of the mount optionally includes one or more or each of the first through third examples, and further includes wherein in a locked configuration of the mount, an end of the shank engages with the terminal end of the lock element to engage the first surface of the lock element with the outer surface of the inner housing. A fifth example of the mount optionally includes one or more or each of the first through fourth examples, and further includes wherein in the locked configuration of the mount, the shank engages with the terminal end of the lock element to engage the slideable element with the inner surface of the arm. A sixth example of the mount optionally includes one or more or each of the first through fifth examples, and further includes wherein the inner housing is rotatable within the outer housing around a first axis, a second axis, and a third axis, with the first, second, and third axes being mutually orthogonal to each other. A seventh example of the mount optionally includes one or more or each of the first through sixth examples, and further includes wherein an end of the arm opposite to the slot includes a bracket adapted to couple to a gantry of a medical imaging system. An eighth example of the mount optionally includes one or more or each of the first through seventh examples, and further includes wherein the outer housing includes a first opening positioned at an end of the outer housing opposite to the lock element, the first opening extending through a thickness of the outer housing in a radial direction of the outer housing. A ninth example of the mount optionally includes one or more or each of the first through eighth examples, and further includes wherein the inner housing includes a second opening positioned at an end of the inner housing opposite to the lock element, the second opening extending through a thickness of the inner housing in a radial direction of the inner housing, where the second opening is adapted to radially align with the first opening. A tenth example of the mount optionally includes one or more or each of the first through ninth examples, and further includes wherein the inner housing includes a clamp adapted to couple an inner surface of the inner housing to a laser diode.

In one embodiment, a medical imaging system comprises: a gantry; an x-ray radiation source; an x-ray radiation detector; and a laser alignment system adapted to indicate a position of a subject to be imaged by the medical imaging system relative to the x-ray radiation source and x-ray radiation detector, the laser alignment system including a plurality of laser mounts coupled to the gantry, with each laser mount moveable relative to the gantry with four degrees of freedom. In a first example of the medical imaging system, the medical imaging system further comprises a plurality of laser radiation sources, and wherein, for each laser mount of the plurality of laser mounts, the laser mount is coupled to a corresponding laser radiation source of the plurality of laser radiation sources, and in an unlocked configuration of the laser mount, the corresponding laser radiation source is moveable relative to the gantry with the four degrees of freedom. A second example of the medical imaging system optionally includes the first example, and further includes wherein, for each laser mount of the plurality of laser mounts, in a locked configuration of the laser mount, the corresponding laser radiation source is not moveable relative to the gantry with the four degrees of freedom. A third example of the medical imaging system optionally includes one or both of the first and second examples, and further includes wherein the four degrees of freedom includes one translational degree of freedom and three mutually orthogonal rotational degrees of freedom.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A medical imaging system, comprising:
    a gantry;
    a laser radiation source; and
    a laser mount including:
        a first section fixedly coupled to the gantry;
        a second section seated within the first section and slideable within the first section; and
        a third section seated within the second section and rotatable within the second section, the third section adapted to house the laser radiation source.

2. The medical imaging system of claim 1, wherein the second section comprises a passage, and wherein the laser mount further comprises a lock element disposed between the second section and the third section with a terminal end of the lock element positioned within the passage, the lock element adapted to lock a position of the third section relative to the second section.

3. The medical imaging system of claim 1, wherein the gantry comprises a housing, and wherein the laser mount is positioned within an interior of the housing.

4. The medical imaging system of claim 1, wherein the third section is rotatable within the second section with three degrees of freedom.

5. The medical imaging system of claim 1, wherein the second section is slideable within the first section with only one degree of freedom, in only a first direction and a second direction opposing the first direction.

6. A medical imaging system, comprising:
    a gantry;
    an x-ray radiation source;
    an x-ray radiation detector; and
    a laser alignment system adapted to indicate a position of a subject to be imaged relative to the x-ray radiation source and x-ray radiation detector, the laser alignment system including a plurality of laser mounts coupled to the gantry, with each laser mount of the plurality of laser mounts moveable relative to the gantry with four degrees of freedom.

7. The medical imaging system of claim 6, further comprising a plurality of laser radiation sources, and wherein, for each laser mount of the plurality of laser mounts, a laser mount is coupled to a corresponding laser radiation source of the plurality of laser radiation sources, and in an unlocked configuration of the laser mount, the corresponding laser radiation source is moveable relative to the gantry with the four degrees of freedom.

8. The medical imaging system of claim 7, wherein, for each laser mount of the plurality of laser mounts, in a locked configuration of the laser mount, the corresponding laser radiation source is not moveable relative to the gantry with the four degrees of freedom.

9. The medical imaging system of claim 6, wherein the four degrees of freedom includes one translational degree of freedom and three mutually orthogonal rotational degrees of freedom.

* * * * *